United States Patent
Kasai et al.

(10) Patent No.: US 8,039,801 B2
(45) Date of Patent: Oct. 18, 2011

(54) DETECTION APPARATUS FOR DETECTING ELECTROMAGNETIC WAVE PASSED THROUGH OBJECT

(75) Inventors: Shintaro Kasai, Yokohama (JP); Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 1041 days.

(21) Appl. No.: 10/584,800

(22) PCT Filed: Dec. 21, 2005

(86) PCT No.: PCT/JP2005/024017
§ 371 (c)(1),
(2), (4) Date: Jun. 28, 2006

(87) PCT Pub. No.: WO2006/070852
PCT Pub. Date: Jul. 6, 2006

(65) Prior Publication Data
US 2009/0134329 A1    May 28, 2009

(30) Foreign Application Priority Data
Dec. 27, 2004   (JP) ................. 2004-376370

(51) Int. Cl.
*G01J 5/02* (2006.01)
(52) U.S. Cl. .................................... 250/341.1
(58) Field of Classification Search ............. 250/358.1, 250/359.1, 360.1, 343, 330–335, 336.1–336.2, 250/337, 338.1–338.5, 339.01–339.15, 340, 250/341.1–341.8
See application file for complete search history.

(56) References Cited

U.S. PATENT DOCUMENTS

| | | | | |
|---|---|---|---|---|
| 3,103,627 A | | 9/1963 | Schneider | 324/58.5 |
| 4,029,416 A | * | 6/1977 | Hawes | 356/51 |
| 4,134,785 A | | 1/1979 | Lavigna et al. | 156/601 |
| 5,174,162 A | * | 12/1992 | Miyake et al. | 73/864.21 |
| 5,521,384 A | * | 5/1996 | Lynch | 250/343 |
| 6,465,776 B1 | * | 10/2002 | Moini et al. | 250/285 |
| 2004/0227089 A1 | * | 11/2004 | Kolodzey et al. | 250/341.8 |
| 2006/0217612 A1 | | 9/2006 | Ouchi | 600/407 |
| 2006/0268945 A1 | | 11/2006 | Minamide et al. | 372/6 |

FOREIGN PATENT DOCUMENTS

| | | |
|---|---|---|
| DE | 2134107 | 1/1972 |
| EP | 0 940 672 A2 | 9/1999 |
| EP | 1 465 286 A1 | 10/2004 |
| GB | 1 327 452 | 8/1973 |
| JP | 2004-317573 | 11/2004 |
| WO | 94/19701 | 9/1994 |
| WO | WO 00/50859 | 8/2000 |

(Continued)

OTHER PUBLICATIONS

E. Nyfors et al., "Industrial Microwave Sensors", Artech House, Inc., © 1989, pp. 1 to 351 (XP-002334964).

(Continued)

*Primary Examiner* — Kiho Kim
(74) *Attorney, Agent, or Firm* — Fitzpatrick, Cella, Harper & Scinto

(57) ABSTRACT

A detection apparatus for detecting electromagnetic waves that have passed through an object is provided which includes a transmission line for transmitting electromagnetic waves therethrough and a detector for detecting electromagnetic waves that have passed through an object, the transmission line having a gap for disposing the object therein.

10 Claims, 9 Drawing Sheets

FOREIGN PATENT DOCUMENTS

| WO | WO 0050859 A1 * | 8/2000 |
| WO | 02/066983 A2 | 8/2002 |

OTHER PUBLICATIONS

European Communication and Search Report, dated Dec. 19, 2007 regarding Application No. 05844596.6-2204 PCT/JP2005024017.

Extended Abstracts, The 51st Spring Meeting, 2004, The Japanese Society of Applied Physics and Related Societies, 28-p-YF-7 (and its partial English translation).

Jiangquan Zhang et al., "Waveguide Terahertz Time-Domain Spectroscopy of Nanometer Water Layers," *Optics Letters*, vol. 29, No. 14, Jul. 15, 2004, pp. 1617-1619.

R. Mendis et al., "THz Interconnect With Low-Loss and Low-Group Velocity Dispersion", *IEEE Microwave and Wireless Components Letters*, vol. 11, No. 11, Nov. 2001, pp. 444-446.

Kanglin Wang et al., "Metal Wire Waveguides for Broadband Terahertz Pulses", *LEOS* 2004, vol. 1, Nov. 2004, pp. 372-373.

R. Mendis et al., "Plastic Ribbon THz Waveguides," *J. Appl. Phys.*, vol. 88, No. 7, Oct. 1, 2000, pp. 4449-4451.

E. Knoesel et al., "Charge Transport and Carrier Dynamics in Liquids Probed by THz Time-Domain Spectroscopy", *Physical Review Letters*, vol. 86, No. 2, Jan. 8, 2001, pp. 340-343.

* cited by examiner

DETECTION APPARATUS FOR DETECTING ELECTROMAGNETIC WAVE PASSED THROUGH OBJECT

TECHNICAL FIELD

The present invention relates to a technique for detecting a change in propagation state of an electromagnetic wave that has passed through an object that is to be inspected or examined (hereinafter, simply referred to as the "object"), and more particularly to a detection apparatus for detecting a change in the propagation state of an electromagnetic wave that has passed through an object to perform measurement, sensing and/or analysis of the object.

BACKGROUND ART

In recent years, attention has been focused on a technique using so-called terahertz-waves. Spectral analysis using terahertz-waves, imaging using terahertz-waves, and the like have been expected for industrial applications.

For example, techniques now under development in application fields of terahertz-waves include an imaging technique using a safe fluoroscopic apparatus as an alternative to an X-ray apparatus, a spectral technique for obtaining an absorption spectrum or complex dielectric constant of a substance to examine a bonding state therein, a technique for analyzing biomolecules, and a technique for estimating a carrier concentration or mobility.

Of the techniques, as a method of spectroscopically analyzing a substance using terahertz-waves, there has been known a method of irradiating a substance to be analyzed with terahertz-waves to obtain a spectrum of transmitted or reflected terahertz-waves.

Meanwhile, water has regions of very strong absorption in the frequency range of 30 GHz to 30 THz. Therefore, terahertz-waves are almost blocked out by, for example, a container with a thickness of 1 mm containing liquid water. Thus, it is relatively difficult to obtain information about a substance contained in water by means of terahertz-waves that have passed through the water.

Therefore, as a method of determining an absorption spectrum or complex dielectric constant of a substance such as water having a strong absorption spectrum band within the terahertz range or molecules contained in such a substance, there has been known a method using an evanescent terahertz-wave which is generated in total reflection in a prism, as disclosed in "Extended Abstracts, The 51st Spring Meeting, 2004, The Japan Society of Applied Physics and Related Societies, 28p-YF-7". In this method, terahertz-waves emitted from a terahertz-wave generator are made incident on a first surface of a prism and totally reflected by a second surface of the prism. Then, terahertz-waves that have exited from a third surface of the prism are detected by a detector, and a sample is disposed on the second surface so as to interact with an evanescent terahertz-wave which is generated upon the total reflection of the terahertz-waves by the second surface, thereby spectroscopically analyzing the sample. According to this method, it is possible to analyze a sample in a form of solid, powder, liquid, or the like. However, because the method disclosed in "Extended Abstracts, The 51st Spring Meeting, 2004, The Japan Society of Applied Physics and Related Societies, 28p-YF-7" uses a spatial optical system, system size reduction as well as optical adjustment is difficult.

DISCLOSURE OF INVENTION

It is, therefore, an object of the present invention to provide a detection apparatus which is capable of easy system size reduction and optical adjustment.

According to a first aspect of the present invention, there is provided a detection apparatus for detecting electromagnetic waves that have passed through an object, comprising a transmission line for transmitting electromagnetic waves therethrough; and a detector for detecting electromagnetic waves that have passed through an object, where the transmission line has a gap for disposing the object therein.

According to a second aspect of the present invention, there is provided a detection method of detecting electromagnetic waves that have passed through an object, comprising the steps of disposing an object in a gap of a transmission line for transmitting electromagnetic waves therethrough; and detecting electromagnetic waves that have passed through the object.

According to a third aspect of the present invention, there is provided a transmission line for transmitting electromagnetic waves therethrough, for use in a detection apparatus for detecting electromagnetic waves that have passed through an object, comprising a gap for disposing an object in the transmission line.

According to the present invention, system size reduction and easy optical adjustment can be realized.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1A is a plan view and FIG. 1B is a perspective view;

BEST MODES FOR CARRYING OUT THE INVENTION

Figure 1A:
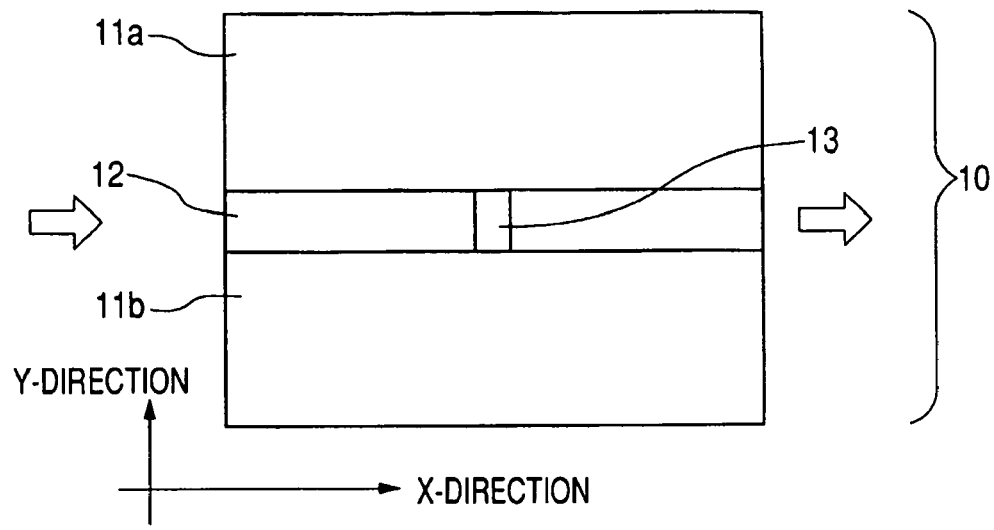
FIGS. 1A and 1B are schematic views showing a detection apparatus in accordance with a preferred embodiment of the present invention.

Hereinafter, the preferred embodiments of the present invention will be more specifically described.

It is preferable that a transmission line for guiding terahertz-waves have a flow path through which a flowable substance such as liquid or powder can be introduced. Any path capable of disposing an object substance to be inspected or examined (hereinafter, simply referred to as an "object substance") in the transmission line may be used. It is preferable that the flow path is not parallel to the propagation direction of the electromagnetic waves and is provided so as to pass through a region of the transmission line in which the electromagnetic waves are strongly distributed. By utilizing the phenomenon that terahertz-waves guided through the transmission line and the flowable substance in the flow path interact with each other to change the propagation state of the terahertz-waves that have passed through the flowable substance, and by comparing propagation states of the terahertz-waves before and after introduction of the flowable substance into the flow path with each other, the physical properties of the flowable substance can be examined or the substance can be identified, for example.

Even for a substance having a terahertz-wave absorbing characteristic like that of water, by designing such that the thickness of the flow path in the propagation direction of the terahertz-waves is small, the terahertz-waves can pass through a sample of such substance.

When a waveguide is used as the transmission line, a gap may be provided at a part of a cladding and a core which compose the waveguide to thereby form a flow path. When a metallic waveguide tube is used as the transmission line, a pipe-shaped hollow member made of a dielectric may be provided in a cavity of a waveguide tube composing the metallic waveguide tube to form a flow path. When a waveguide tube used is filled with a dielectric, a gap may be provided in a portion of the dielectric to form a flow path. When a transmission cable is used as the transmission line, a gap may be provided at a part of a dielectric portion between a ground cable and a signal cable which compose the transmission cable to form a flow path.

When a metallic waveguide tube used as the transmission line has a cavity therein, a pipe-shaped hollow member made of a dielectric can be provided in the cavity to form a flow path. In such a case, it is desirable that the pipe-shaped hollow member constituting the flow path is a dielectric with low loss, low dispersion and a low refractive index. Further, when a metallic waveguide tube is internally filled with a dielectric and a gap is provided in a portion of the dielectric to form a flow path, it is desirable that the dielectric has low loss, low dispersion and a low refractive index. By forming such a flow path, even when only a small amount of sample is obtained, measurement can be performed. Further, by forming a flow path that is shielded from outside air, it is possible to sense a substance which is susceptible to influence by outside air.

Terahertz-waves may be coupled from the outside into a transmission line, while a terahertz-wave generator may be integrated in a portion of a transmission line. For example, when a waveguide or a waveguide tube is used, a terahertz-wave generator may be integrated at an end surface of the waveguide or the waveguide tube. When a transmission cable is used, a terahertz-wave generator may be integrated on the transmission cable. Further, similarly, terahertz-waves propagating through a transmission line may be radiated outside and detected by a terahertz-wave detector, while a terahertz-wave detector may be integrated in a portion of a transmission line. In such a case, there are advantages that the terahertz-waves are not influenced by moisture in air, optical adjustment is unnecessary, and size reduction can be realized.

Examples of the terahertz-wave generator and terahertz-wave generating method include a method of applying a voltage to a photoconductive antenna formed on gallium arsenide formed by a low-temperature growth method and irradiating a femtosecond laser light pulse thereon. Examples of integration of a terahertz-wave generator include a method in which such a photoconductive antenna as mentioned above is provided on, for example, an end surface of a waveguide tube. Further, examples of the terahertz-wave detector include one utilizing a method of irradiating a femtosecond laser light pulse onto a photoconductive antenna without applying a voltage thereto and measuring the resulting current. As another example of the integration of a terahertz-wave detector, the above-mentioned photoconductive antenna may be provided on an end surface of a waveguide tube from which terahertz-waves exit. Thereby, sensing can be performed while preventing the terahertz-waves from being influenced by moisture in the air.

Moreover, there may be employed a method in which an electrooptic crystal having an electrooptic ("EO") effect (such as ZnTe) is provided on an end surface from which terahertz-waves exit, and the crystal orientation of the EO crystal and the polarization direction of the terahertz-waves are suitably selected, thereby utilizing a phenomenon in which the reflectance and refractive index of the EO crystal are changed with polarization dependence.

In addition, as another example of integration method of a terahertz-wave generator, a nonlinear substance (such as DAST crystal) may be provided inside or at an end surface of a waveguide tube or waveguide.

Further, when it is necessary to take a sample at a separate position as in the case of, for example, blood, by connecting a sampling tool (such as a needle for syringe) as means for obtaining an object and the flow path as connecting means for connecting the obtained object to a path through another flow path (such as a tube), the sample can be set at a predetermined position simultaneously with sampling. In addition, because an area of the sample in the flow path which is in contact with outside air is small, such configuration is advantageous in the case where a sample susceptible to outside air is to be measured.

When specific (one or more kinds of) particles or molecules contained in a flowable sample are to be sensed, by introducing the flowable sample from one end of a flow path and providing on the other end thereof a filter (for example, a semipermeable membrane) which does not allow passing of the specific particles or molecules but allows passing of other flowable substances (such as water), sensing can be performed while increasing the concentration of the specific particles or molecules in the sensing portion. This method makes it possible to perform sample concentration and sensing either successively or simultaneously, and is therefore advantageous for improving working efficiency.

Moreover, by disposing on a wall surface of a flow path a substance which absorbs or is bonded to specific (one or more kinds of) particles or molecules contained in a flowable substance, and by capturing the specific particles or molecules on the wall surface of the flow path, it is possible to sense a flowable sample and particles or molecules contained therein based on a change in the complex dielectric constant or absorption spectrum of the substance disposed on the wall surface of the flow path resulting from the absorption or bonding of the particles or molecules.

Moreover, as the electromagnetic waves, it is preferable to use electromagnetic waves including an arbitrary component in a frequency range of 30 GHz to 30 THz.

Hereinafter, the preferred embodiments of the present invention will be described with reference to the accompanying drawings.

First Embodiment

A first embodiment of the present invention will be described with reference to FIGS. 1A, 1B, and FIG. 2. A parallel plate waveguide 10 has a structure in which a polystyrene plate 12 is interposed between metallic plates 11a, 11b. The polystyrene plate 12 has a gap 13 provided therein. The interval between the opposed surfaces of the metallic plates 11a, 11b is about 100 µm. A typical size of each of the metallic plates 11a, 11b is about 10 mm to 20 mm in each of the x-direction and the z-direction. The gap 13 is about 50 µm in the x-direction. A flowable sample such as a fluid can be introduced into the gap 13. In this embodiment, the interval between the metallic plates 11a, 11b is set to 100 µm, but the present invention is not limited to that value. Accordingly, the gap includes a flow path having a dimension of cross-section smaller than that of a transmission line for passing the terahertz-waves. Further, although polystyrene is used for the member interposed between the metallic plates 11a, 11b, the present invention is not limited to that example. For the member interposed between the metallic plates 11a, 11b, any other dielectric (resin or semiconductor) may be used as long as it is sufficiently small in absorption (loss) and dispersion with respect to the terahertz-waves. Moreover, it is desirable that the refraction index is close to 1. Further, a semiconductor having a high conductivity may be used instead of the metallic plates 11a, 11b.

Figure 1B:
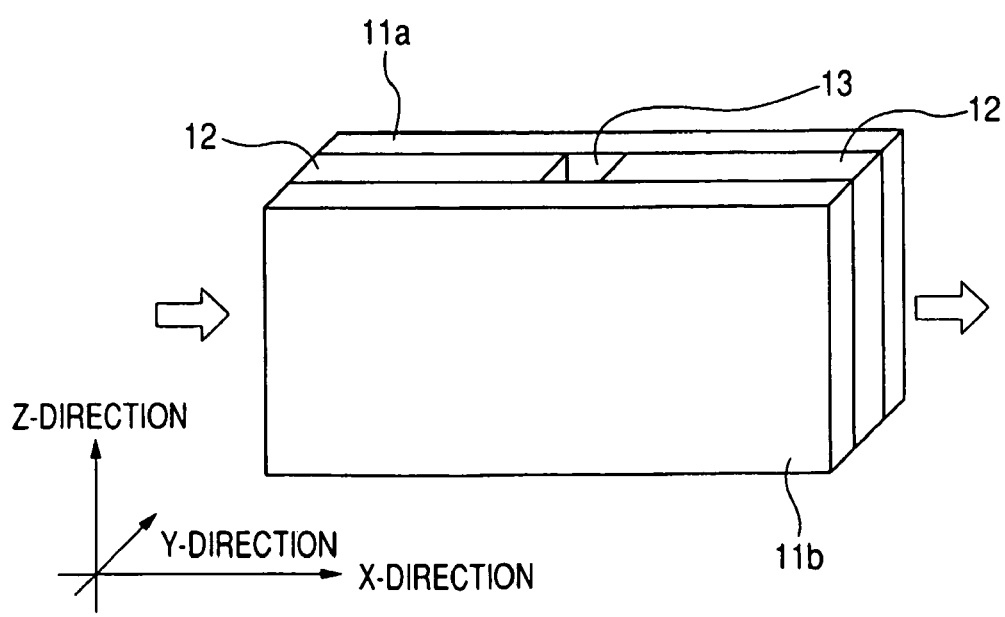
Figure 2:
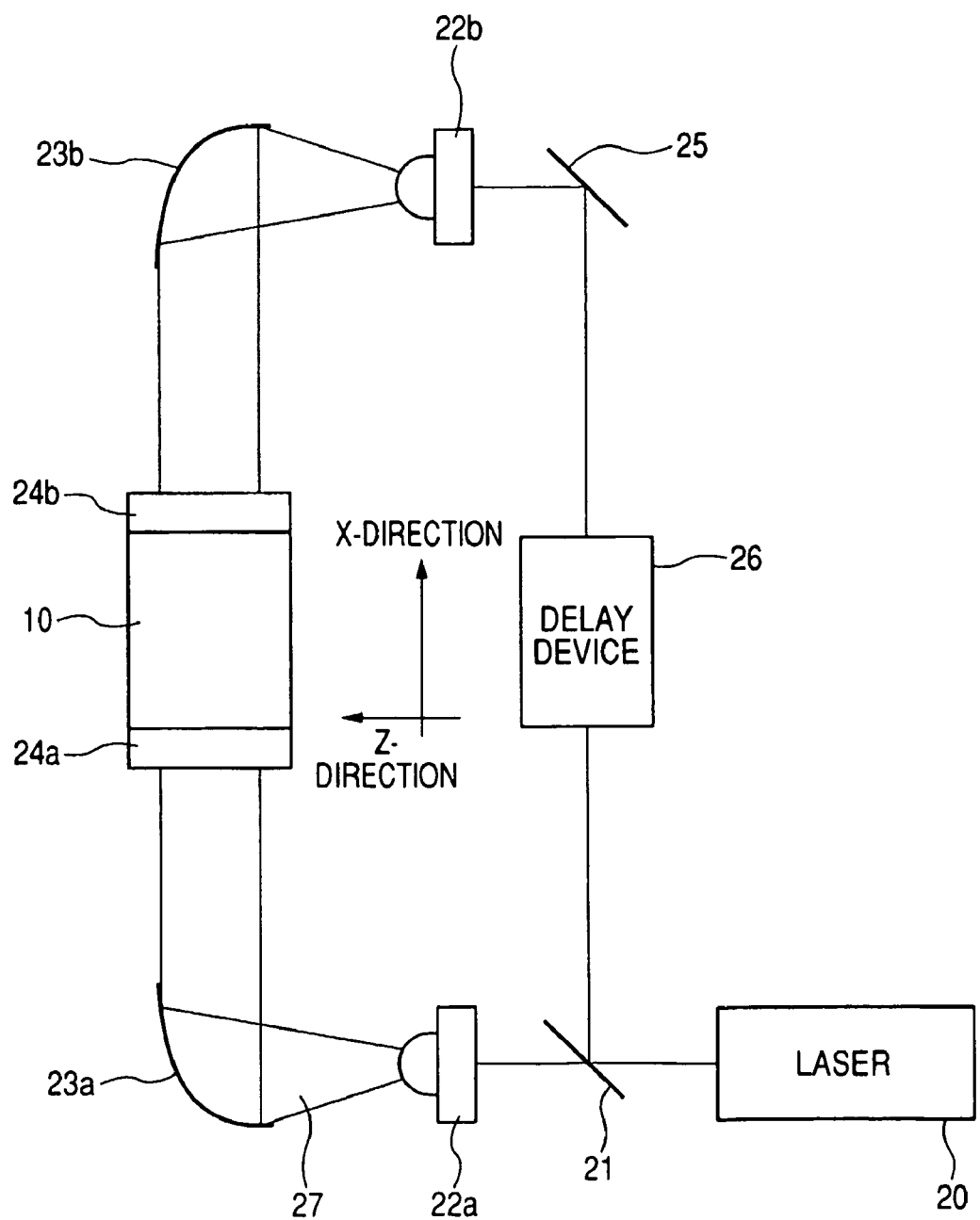
FIG. 2 is a schematic diagram showing a detection apparatus in accordance with a preferred embodiment of the present invention.

In FIGS. 1A and 1B, terahertz-waves enter the parallel plate waveguide 10 in a direction indicated by the left-hand arrow in the figures and exit from the parallel plate waveguide 10 in a direction indicated by the right-hand arrow in the figures. The terahertz-waves propagating through the parallel plate waveguide 10 interact with a flowable sample introduced into the gap 13. By utilizing the phenomenon that the spectrum or propagation state of the terahertz-waves that have passed through the parallel plate waveguide 10 changes as a result of the introduction of the flowable sample into the gap 13, the flowable substance can be measured, sensed, or analyzed.

Hereinafter, an entire sensing system will be described with reference to FIG. 2. A beam of laser light pulses having a pulse width of about 100 fs (femtoseconds) emitted from a femtosecond laser 20 is split by a beam splitter 21 into two beams following different optical paths, one beam being irradiated onto a biased gap portion of a photoconductive antenna 22a made of low-temperature grown GaAs (LT-GaAs) or the like to generate terahertz-wave pulses 27 (a hemispherical lens made of high-resistance Si or the like being in close contact with a rear surface of the photoconductive antenna). The terahertz-wave pulses 27 are reflected by a parabolic mirror 23a, pass through a semicylindrical lens 24a made of high-resistance Si (for example, 10 kΩ·cm) or the like and are coupled to the parallel plate waveguide 10 at a first end of the parallel plate waveguide 10. The terahertz-wave pulses interact with the sample (not shown) introduced into the gap 13 of the parallel plate waveguide 10 and then exit from a second end of the parallel plate waveguide 10 and reach a photoconductive antenna 22b through a semicylindrical lens 24b and a parabolic mirror 23b. The other beam produced by the beam splitter 21 passes through a time delay device 26, is reflected by a mirror 25 and reaches the photoconductive antenna 22b simultaneously with the arrival of the terahertz-wave pulses. At this time, by shifting the timing of the laser light beam reaching the photoconductive antenna 22b through the time delay device 26 and the timing of the terahertz-wave pulses reaching the photoconductive antenna 22b through the parallel plate waveguide 10 from each other by use of the time delay device 26, the waveform of the terahertz-wave pulse can be obtained. When the femtosecond laser light beam passing through the time delay device 28 is irradiated onto the photoconductive antenna 22b, a current flows through the photoconductive antenna 22b for a period which corresponds to the pulse time width of the femtosecond laser and to a carrier life of a semiconductor film constituting the photoconductive antenna 22b. The magnitude of the current at this time reflects the magnitude of electric field amplitude of the terahertz-wave pulse 27 incident on the photoconductive antenna 22b. Therefore, measuring the current that flows through the photoconductive antenna makes it possible to obtain the waveform of the terahertz-wave pulse 27, which is then processed by means of a Fourier transform to give a spectrum of the terahertz-wave pulse 27.

The parallel plate waveguide can transmit electromagnetic waves in a TEM mode. Therefore, when no sample exists in the gap 13, the terahertz-wave pulses 27 propagate through the parallel plate waveguide 10 without a change in the pulse waveform occurring due to the parallel plate waveguide 10. That is, when no sample exists in the gap 13, the waveform of the terahertz-wave pulse 27 before incidence on the parallel plate waveguide 10 and the waveform of the terahertz-wave pulse 27 after passing through the parallel plate waveguide 10 are substantially similar to each other.

Because the gap 13 has such a sufficiently small thickness as about 50 µm in the x-direction, even when the gap 13 is filled with a sample which absorbs terahertz-waves well, such as water, the terahertz-wave pulses propagating through the parallel plate waveguide 10 can pass through the gap 13 without being completely absorbed.

Figure 3A:
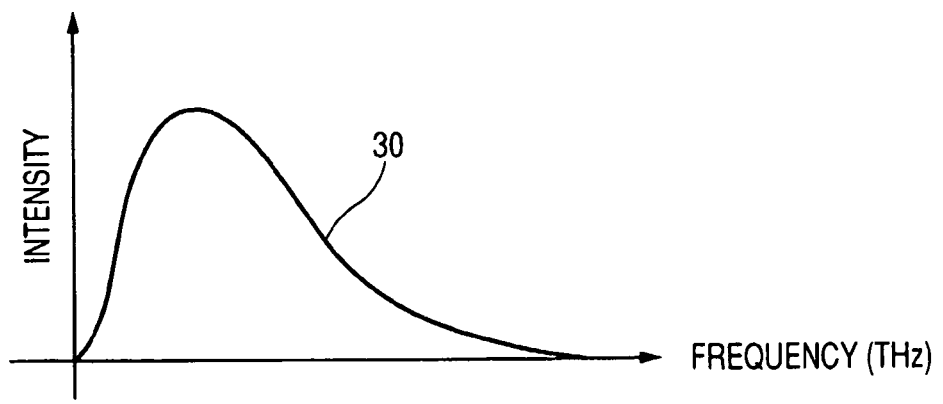
FIGS. 3A, 3B, and 3C are schematic graphical representations each showing a change in state of an electromagnetic wave obtained by a detection apparatus in accordance with a preferred embodiment of the present invention.
Figure 3B:
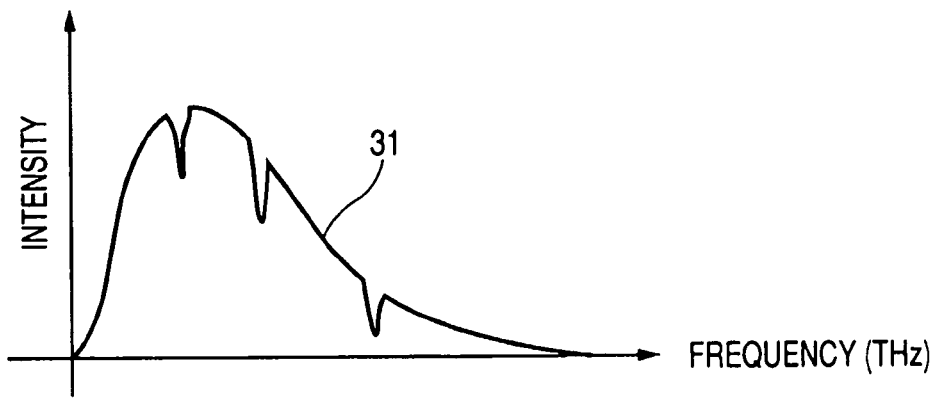
Figure 3C:
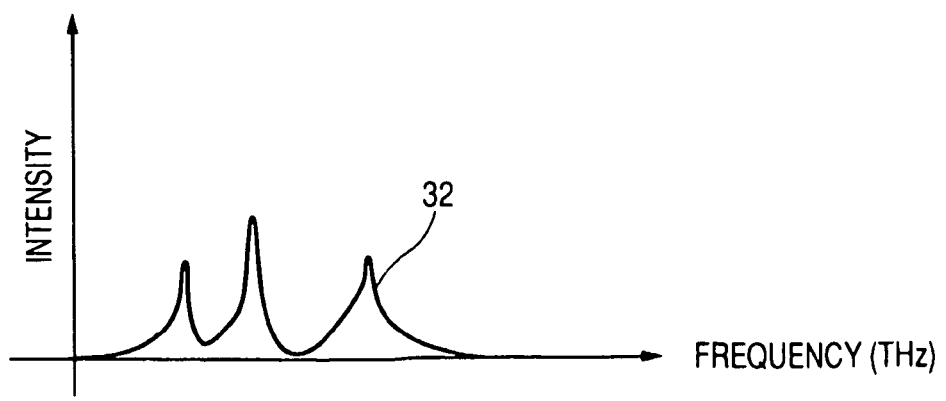

Next, a measurement example in this embodiment will be specifically described with reference to FIGS. 3A, 3B, and 3C. FIGS. 3A, 3B, and 3C are schematic graphical representations showing spectra of the terahertz-waves which are obtained in the embodiment of the present invention. First, in a state in which a flowable sample is not introduced into the gap 13 as shown in FIGS. 1A and 1B, the waveform of the terahertz-wave pulses passing through the parallel plate waveguide 10 is recorded and subjected to a Fourier transform to obtain a power spectrum 30 (FIG. 3A). Next, in a state in which a flowable sample is introduced into the gap 13, the waveform of the terahertz-wave pulses that have passed through the parallel plate waveguide 10 is recorded and subjected to a Fourier transform to obtain a power spectrum 31 (FIG. 3B). By determining the ratio between the power spectra 30 and 31, an absorption spectrum 32 of the flowable sample to the terahertz-waves is obtained (FIG. 3C).

In this method, the volume of the gap 13 is sufficiently small and only a slight amount of sample is required. Therefore, this method is advantageous in a case where an expensive sample (for example, a solution containing an antibody) is to be examined.

Further, in this embodiment, the terahertz-wave pulse generation has been described by taking as an example a method using a photoconductive antenna. However, there may also be used other methods such as a method of radiating a nonlinear crystal with a femtosecond laser light or a method using parametric oscillation. Moreover, as the detection method, there may also be used, for example, a known method using an electrooptic crystal.

Second Embodiment

Figure 4:
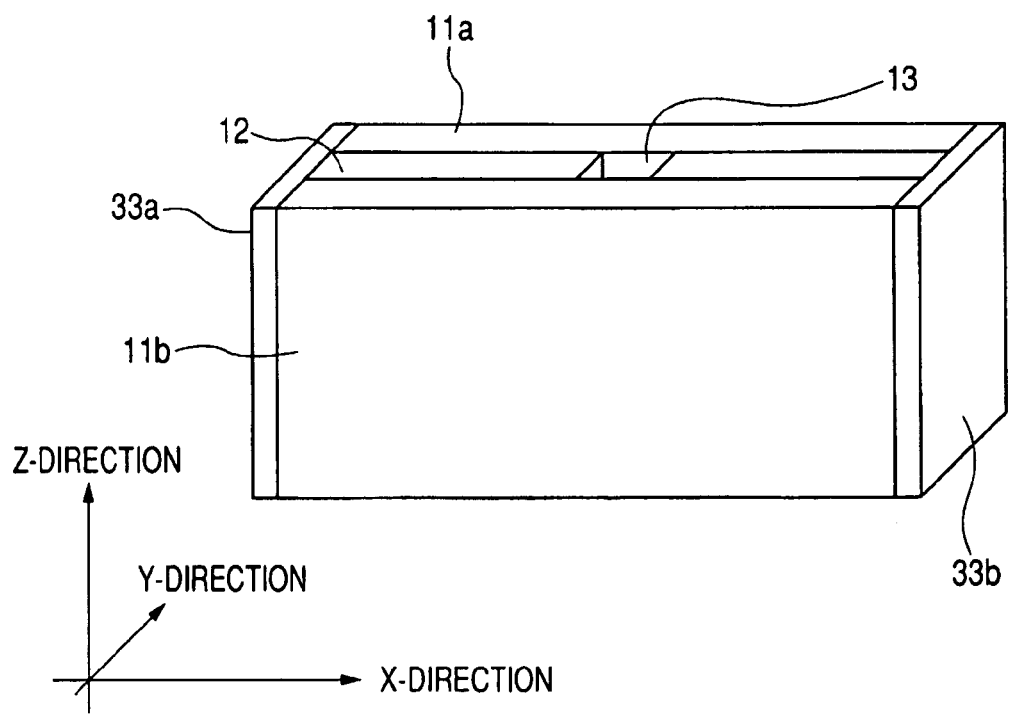
FIG. 4 is a schematic perspective view showing a detection apparatus in accordance with a preferred embodiment of the present invention.

A second embodiment of the present invention will be described with reference to FIGS. 4 and 5. In the second embodiment of the present invention, as shown in FIG. 4, photoconductive antennas 33a, 33b are provided in both ends of the parallel plate waveguide 10. However, in this embodiment, unlike the first embodiment, a hemispherical lens made of high-resistance Si or the like is not in close contact with the photoconductive antennas 33a, 33b. In this case, it is unnecessary to perform optical axis alignment of the terahertz-wave spatial propagation optical system, and consequently the size reduction of the system can be attained.

The photoconductive antennas 33a, 33b each typically have a substrate with a size of about several millimeters to one centimeter in each of the y- and the z-directions and are each provided with an antenna pattern (not shown) on its outer surface. Typical sizes of the metallic plates 11a, 11b, the polystyrene plate 12, and the gap 13 are identical to those described in the first embodiment. When the length (thickness) of each of the metallic plates 11a, 11b in the y-direction is set to about 5 or more millimeters, the photoconductive antennas 22a, 22b can be provided in both ends of the parallel plate waveguide 10.

Figure 5:
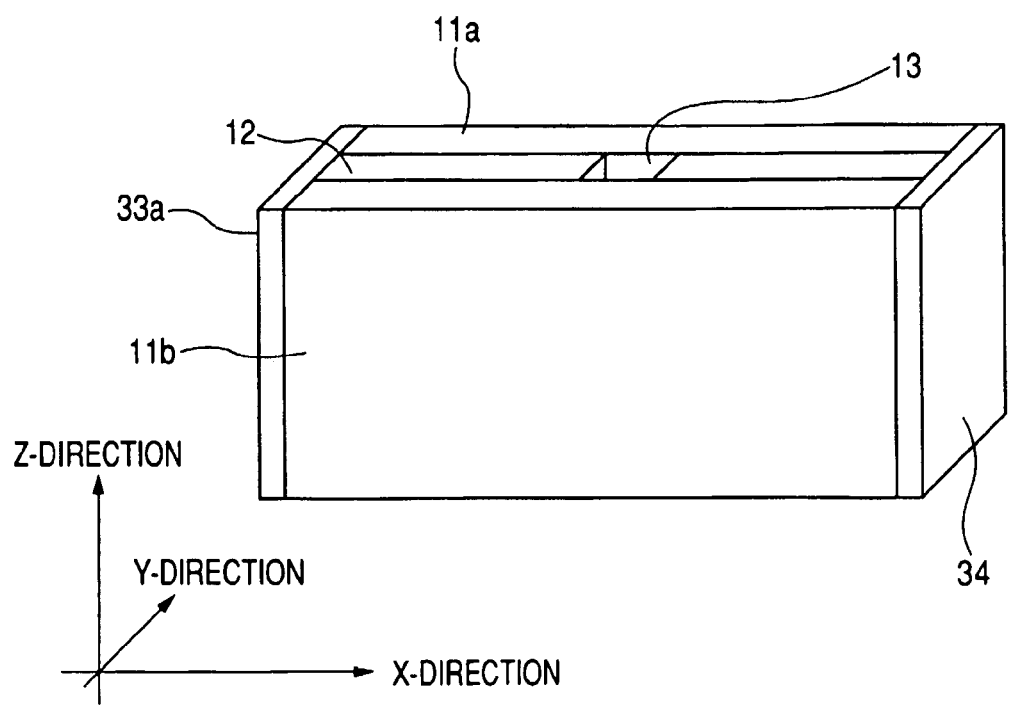
FIG. 5 is a schematic perspective view showing a detection apparatus in accordance with a preferred embodiment of the present invention.

Alternatively, as shown in FIG. 5, a photoconductive antenna 33a and an EO crystal 34 which is a substance having an electrooptic effect (such as ZnTe) may be provided in the respective ends of the parallel plate waveguide 10. In this case, the terahertz-wave pulses are detected using a known technique of utilizing a phenomenon in which when terahertz-waves generated by irradiating a femtosecond laser onto the photoconductive antenna 33a pass through the gap 13 and then reach the EO crystal 34, the reflectance of the EO crystal 34 to the laser light varies depending on the wave amplitude of the terahertz-waves that have reached the crystal, thereby permitting the user to obtain the amplitude of the terahertz-waves.

Alternatively, a nonlinear optical crystal such as a DAST crystal or InP may be provided at an end of the parallel plate waveguide 10 instead of the photoconductive element 33a. In this case, irradiating such a nonlinear optical crystal directly with a femtosecond laser beam generates terahertz-wave pulses.

Third Embodiment

Figure 6A:
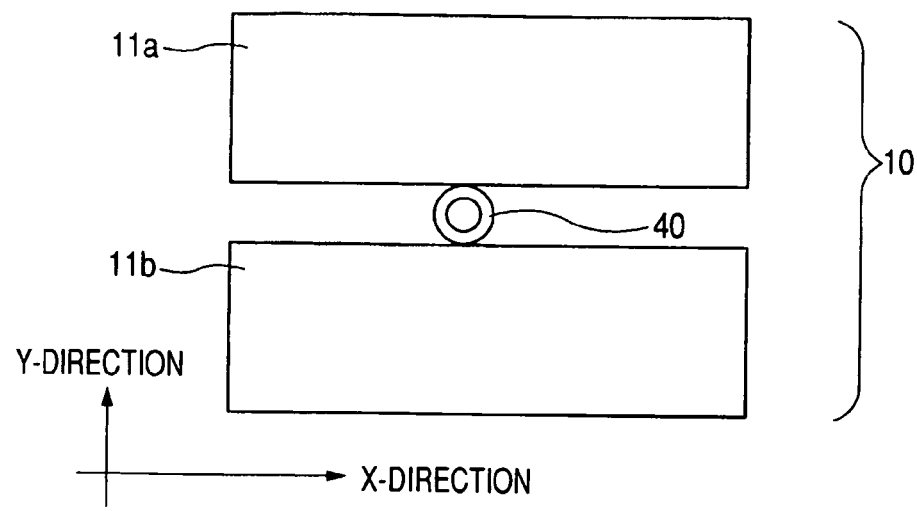
FIGS. 6A and 6B are schematic views showing a detection apparatus in accordance with a preferred embodiment of the present invention, FIG. 6A being a plan view and FIG. 6B a front view.
Figure 6B:
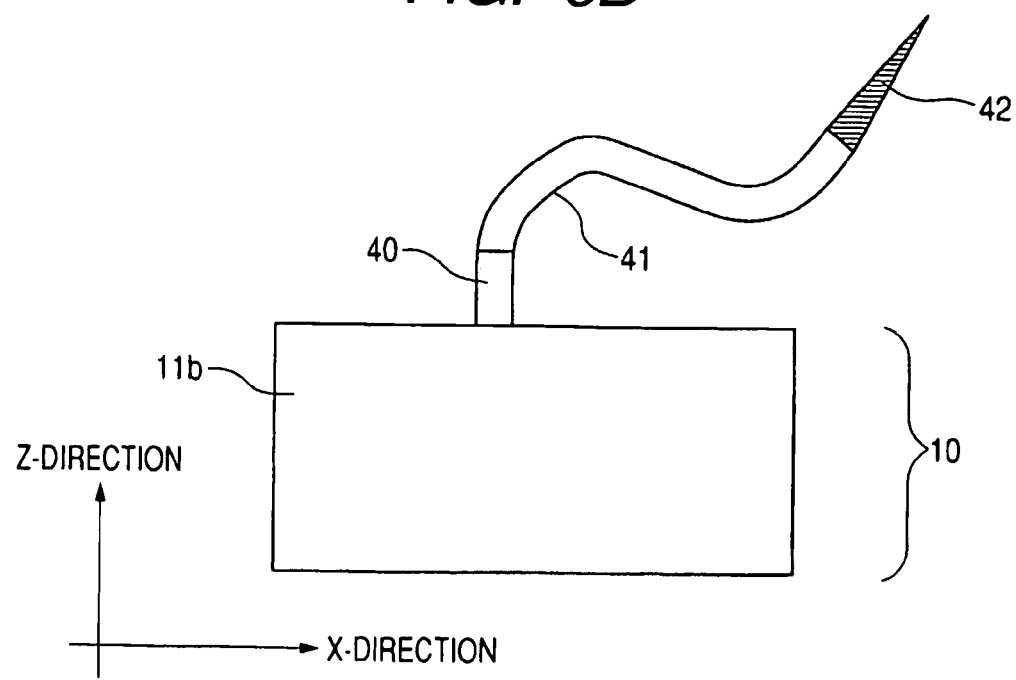

A third embodiment of the present invention will be described with reference to FIGS. 6A and 6B. The detection apparatus in accordance with this embodiment has a structure in which a hollow member 40 made of a substance with less absorption/loss and dispersion in the terahertz-wave frequency band, such as polystyrene, is interposed between metallic plates 11a, 11b composing the parallel plate waveguide 10. With this structure, for example, when an end of the hollow member 40 is connected to a tube 41 and another end of the tube 41 is connected to a needle for syringe 42, a blood sample is taken from a human body and simultaneously introduced into the waveguide, so that a terahertz transmission spectrum of the blood can be easily obtained.

With this embodiment, it is possible to successively perform the sampling of a flowable sample and the measurement, sensing, and analysis of the sample.

Fourth Embodiment

Figure 7:
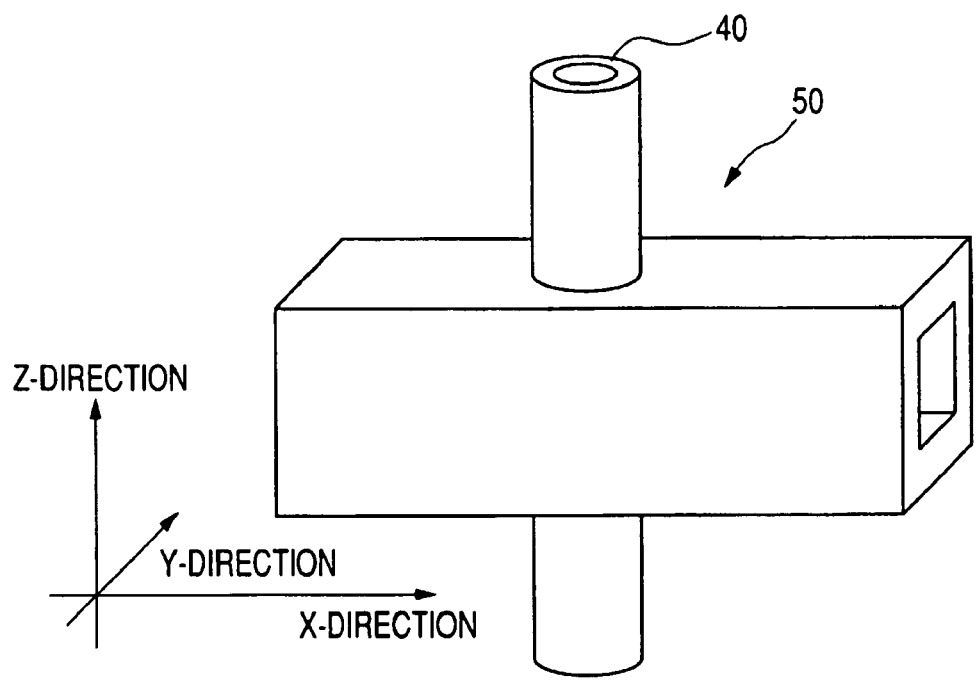
FIG. 7 is a schematic perspective view showing a detection apparatus in accordance with a preferred embodiment of the present invention.
Figure 8:
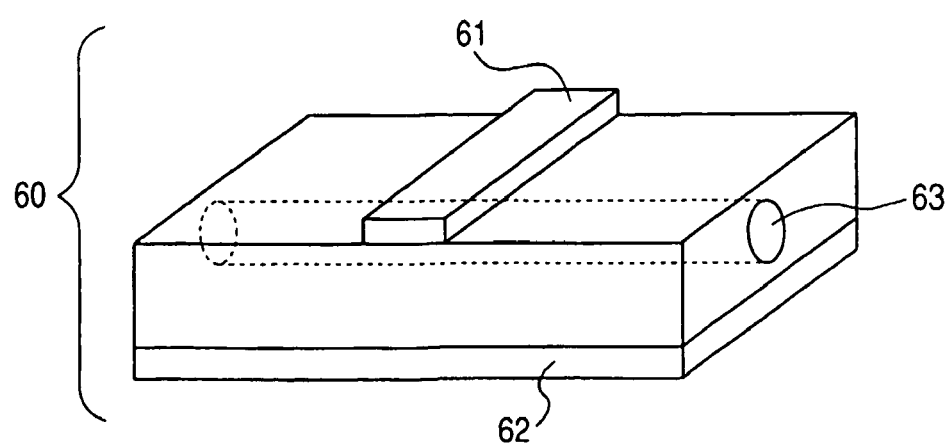
FIG. 8 is a schematic perspective view showing a detection apparatus in accordance with a preferred embodiment of the present invention.

A fourth embodiment of the present invention will be described with reference to FIGS. 7 and 8. In the fourth embodiment, a waveguide tube whose section is square or circular is used instead of the parallel plate waveguide. As shown in FIG. 7, a hollow member 40 for flowable sample introduction is provided in a waveguide tube 50 having a square section. A typical size of the section of the square waveguide tube is 100 µm to 200 µm in each of the y- and the z-directions. When such a waveguide tube is used, there is an advantage that size reduction can be realized as compared with the case where the parallel plate waveguide is used.

Further, a gap capable of introducing a flowable sample may be provided between a signal cable and a ground cable of a transmission cable. As shown in FIG. 8, a flow path 63 is provided between a signal cable 61 and a ground cable 62 of a transmission cable 60 (microstrip line in the example shown in the figure). When the flow path is provided in the transmission cable, the sample introducing flow path and the terahertz-waveguide portion (transmission cable) can be integrally formed on the same substrate, so that further size reduction can be realized.

Fifth Embodiment

Figure 9:
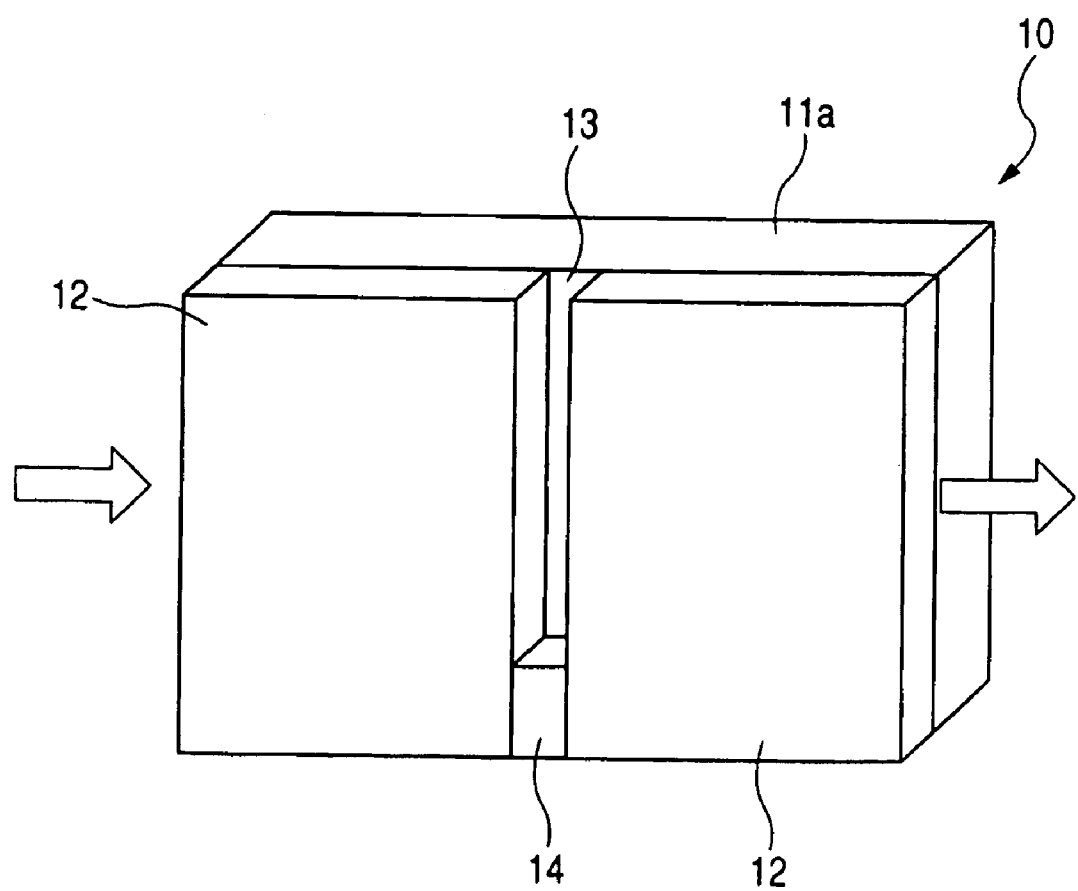
FIG. 9 is a schematic perspective view showing a detection apparatus in accordance with a preferred embodiment of the present invention.

A fifth embodiment of the present invention will be described with reference to FIG. 9. In a parallel plate waveguide 10 having a gap 13 such as described in the first embodiment, a filter 14 is provided in a portion of the gap 13. In FIG. 9, a metallic plate 11b as illustrated in FIGS. 1A and 1B is omitted for convenience of description. In the figure, terahertz-waves enter the parallel plate waveguide 10 in a direction indicated by the left-hand arrow and exit from the parallel plate waveguide 10 in a direction indicated by the right-hand arrow. Here, it is assumed that an end of the gap 13 at which the filter 14 is provided is a first end of the gap 13 and an end opposed to the first end is a second end of the gap 13. For example, when a certain type of protein contained in a body fluid is to be sensed, a filter (for example, a semipermeable membrane) which allows the passing of water but does not allow the certain type of protein to pass is provided. When the body fluid is continuously caused to flow into the gap 13 from the second end, the concentration of the certain type of protein in the gap 13 increases, so that a transmission spectrum of the certain type of protein can be measured at a high sensitivity with a high precision.

With this structure, sample concentration increase and sensing can be performed in the same portion, so that it is possible to omit work such as sample transfer.

Sixth Embodiment

Figure 10:
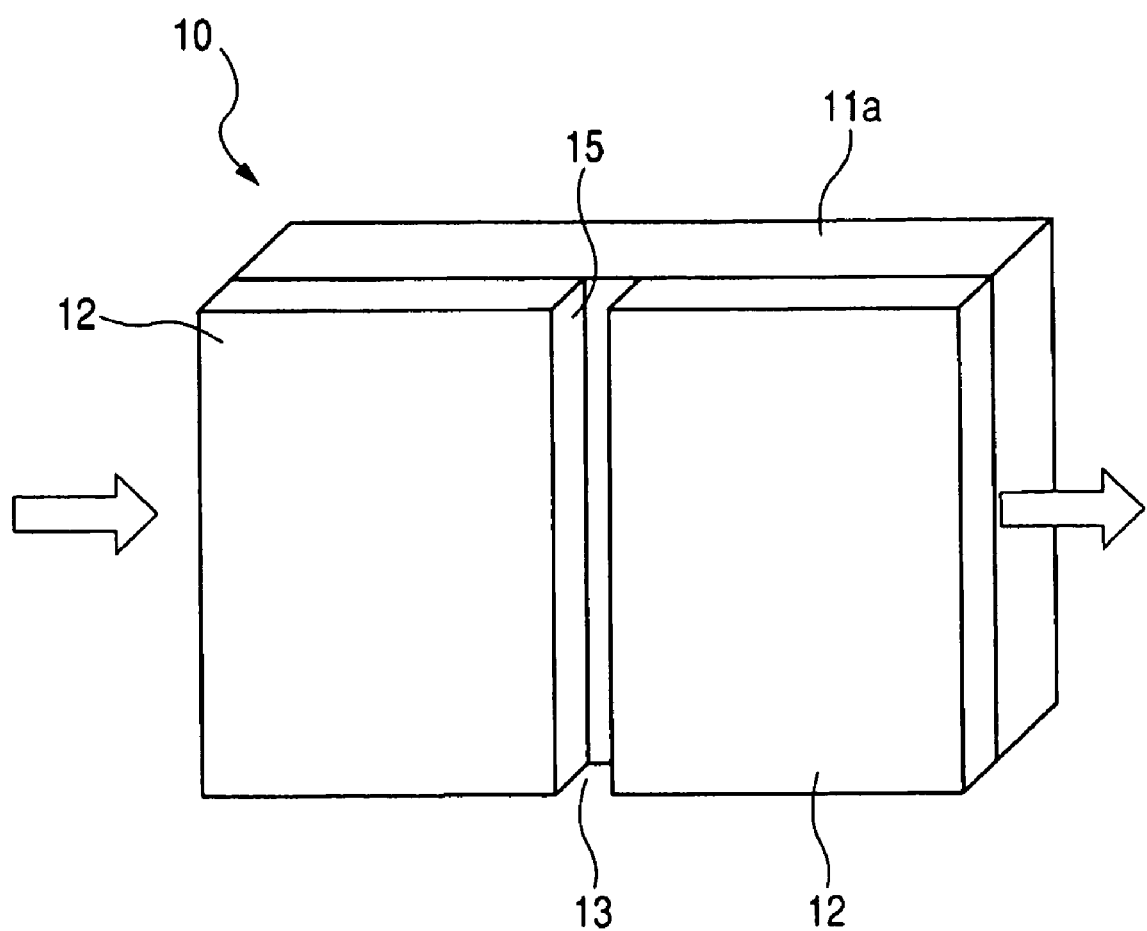
FIG. 10 is a schematic perspective view showing a detection apparatus in accordance with a preferred embodiment of the present invention.

A sixth embodiment of the present invention will be described with reference to FIG. 10. In a parallel plate waveguide 10 having a gap 13 such as described in the first embodiment, a first substance 15 (e.g., biotin) which is specifically bonded to or absorbs a given substance in a solution is applied to the inner surface of the gap 13. In FIG. 10, a metallic plate 11b as illustrated in FIGS. 1A and 1B is omitted for convenience of description. In the figure, a terahertz-wave enters the parallel plate waveguide 10 in a direction indicated by the left-hand arrow and exits from the parallel plate waveguide 10 in a direction indicated by the right-hand arrow. A solution containing a second substance (e.g., avidin; not shown) which is specifically bonded to the first substance 15 is flown into the gap 13. The second substance in the solution is bonded to the first substance 15 applied to the inner surface of the gap 13, so that the complex dielectric constant and the absorption spectrum of the first substance 15 in the frequency range of the terahertz-waves are changed, based on which the second substance can be sensed at a high sensitivity. With this structure, in addition to the high-sensitivity sensing of a given substance, it is possible to distinguish between a substance which is non-specifically absorbed to the substance 15 and a substance which is specifically absorbed to the substance 15 based on the spectrum of the transmitted terahertz-waves.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2004-376370 filed on Dec. 27, 2004, the entire content of which is hereby incorporated by reference herein.

The invention claimed is:

1. A detection apparatus for detecting electromagnetic terahertz waves that have passed through an object, comprising:
   a transmission line for transmitting electromagnetic terahertz waves there through, the transmission line having a gap therein; and
   a detector for detecting electromagnetic terahertz waves that have passed through an object disposed in the gap,
   wherein the gap comprises a flow path for introducing the object into the transmission line,
   wherein the transmission line and the flow path cross each other, and
   wherein the flow path is a unidirectional and continuous flow path and the dimension of cross-section of the flow path is smaller than that of the transmission line.

2. The detection apparatus according to claim 1, which comprises a plurality of such detectors.

3. The detection apparatus according to claim 1, further comprising means for obtaining the object.

4. The detection apparatus according to claim 1, further comprising a generating means for generating the terahertz waves.

5. The detection apparatus according to claim 1, wherein the flow path has a filter which does not allow passing of specific particles or molecules but allows passing of other flowable substances, and wherein the object is the specific particles or molecules.

6. A detection apparatus for detecting terahertz waves that have passed through an object, comprising:
   a generating part for generating terahertz waves;
   a transmission line, for transmitting the terahertz waves therethrough;
   a detector for detecting terahertz waves that have propagated through the transmission line;
   a path for disposing the object at a part of a region in the transmission line through which terahertz waves pass when the terahertz waves propagate through the transmission line; and
   means for obtaining the object,
   wherein terahertz waves that have passed through the object disposed in the path are detected by the detector,
   wherein the path is a unidirectional and continuous flow path and the dimension of cross-section of the flow path is smaller than that of the transmission line,
   wherein the means for obtaining the object is a sampling tool for guiding the object to the path or taking the object out of the path, and
   wherein the transmission line and the flow path cross each other.

7. The detection apparatus according to claim 6, wherein the transmission line is one of the waveguide and the waveguide tube, wherein the waveguide tube is a metal waveguide tube and wherein the waveguide is a parallel plate waveguide comprising metal plates.

8. The detection apparatus according to claim 6, wherein the means for obtaining the object further comprises a connecting means for connecting the sampling tool and the path.

9. The detection apparatus according to claim 8, wherein the connecting means is a tube.

10. The detection apparatus according to claim 6, wherein the sampling tool is a needle for a syringe.

* * * * *